United States Patent [19]
Sheehan

[11] Patent Number: 5,009,275
[45] Date of Patent: Apr. 23, 1991

[54] MEDICAL SWAB WEIGHING APPARATUS

[76] Inventor: James Sheehan, The Hermitage, Blackrock, County Dublin, Ireland

[21] Appl. No.: 440,972

[22] Filed: Nov. 22, 1989

[30] Foreign Application Priority Data

Nov. 24, 1988 [IE] Ireland ............................. 3527/88

[51] Int. Cl.$^5$ ..................... G01G 19/42; G01G 19/52
[52] U.S. Cl. ............................. 177/25.13; 177/25.19; 177/245
[58] Field of Search ................. 177/25.13, 25.19, 165, 177/245

[56] References Cited
U.S. PATENT DOCUMENTS

| | | | |
|---|---|---|---|
| 3,367,431 | 2/1968 | Baker | 177/245 X |
| 4,295,537 | 10/1981 | McAvinn et al. | 177/165 X |
| 4,422,548 | 12/1983 | Cheesman et al. | 177/245 X |
| 4,478,332 | 10/1984 | Wiestmiller | 206/363 X |
| 4,650,464 | 3/1987 | Ruiz et al. | 177/25.13 X |

Primary Examiner—George H. Miller, Jr.
Attorney, Agent, or Firm—Ladas & Parry

[57] ABSTRACT

A medical swab weighing apparatus for calculating blood loss comprises a container means for receiving swabs, the container means being removably mountable on a weighing means. The weighing means has a storage means for storing the weight of a dry swab. A programmed microprocessor is provided for calculating the weight of blood absorbed in a used swab each time a used swab is deposited in the container means.

8 Claims, 4 Drawing Sheets

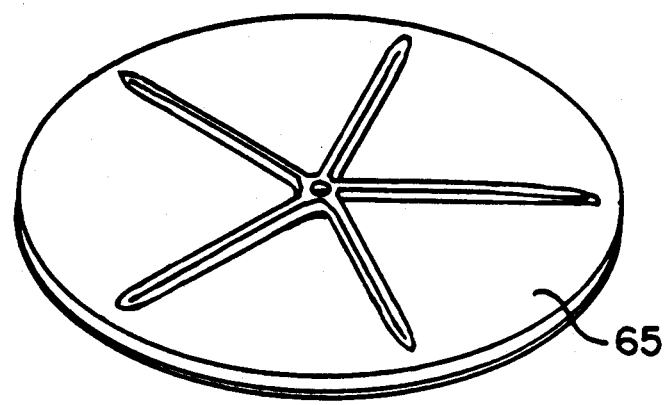
FIGURE 5
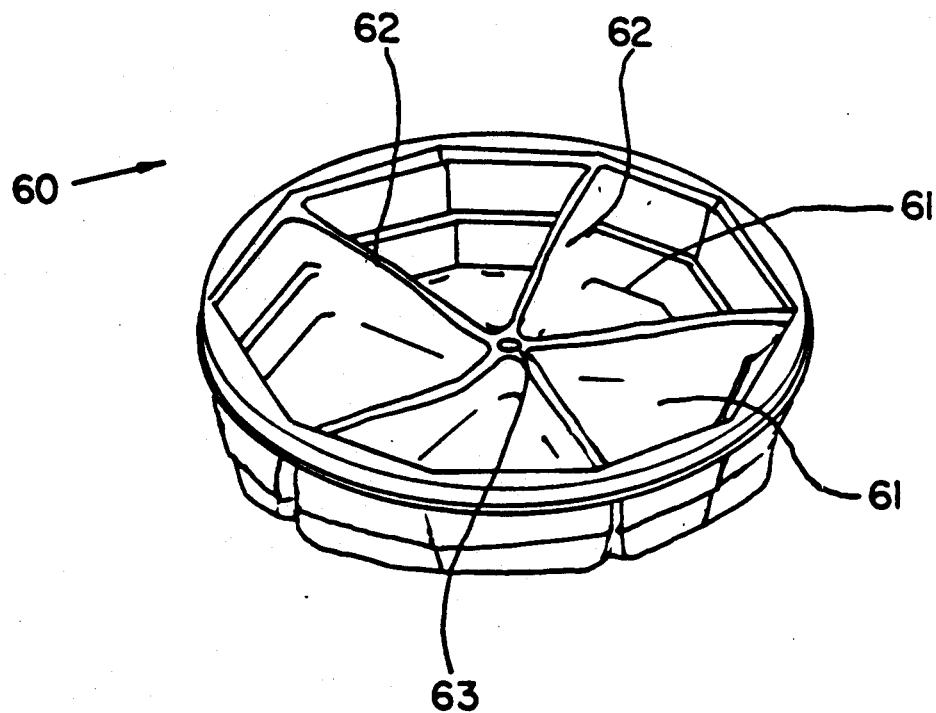

MEDICAL SWAB WEIGHING APPARATUS

The present invention relates to a medical swab weighing apparatus.

During surgical operations it is an essential requirement that medical staff count the number of swabs provided for an operation, and also count the number of used swabs after the operation, to ensure that no swabs have been left inside a patient. It is also necessary for medical personnel to weigh the swabs (or at least know the dry weight in advance) prior to use, and also to weigh the swabs after use so that the blood weight absorbed by the swabs, which is lost by the patient, can be calculated.

According to the present invention there is provided a medical swab weighing apparatus for calculating blood loss comprising, container means for receiving swabs, said container means being removably mountable on a weighing means, the weighing means having storage means for storing the weight of a dry swab, and program means for calculating the weight of blood absorbed in a used swab each time a used swab is deposited in the container means.

Preferably, the weighing apparatus further comprises means for determining and providing an indication of the number of swabs deposited in said container means.

The weighing apparatus preferably comprises a housing having a weighing plate connected to an electrically controlled load cell mounted within the housing, the output signal from the load cell being fed to a microprocessor via an analogue to digital converter. A keypad is preferably mounted on the housing for controlling the operation of the microprocessor. The housing is preferably provided with suitable visual displays for indicating the weight of blood loss and the number of swabs in the container means.

The container means preferably comprises a container having a plurality of radially disposed compartments each for receiving a used swab. The container preferably comprises a translucent or transparent plastics material.

The container and the weighing apparatus preferably have interengaging surfaces to securely locate the container on the weighing apparatus.

Embodiments of the invention will now be described, by way of example, with reference to the accompanying drawings, in which;

FIG. 5 is a perspective view of another container and lid according to the invention.

Figure 2:
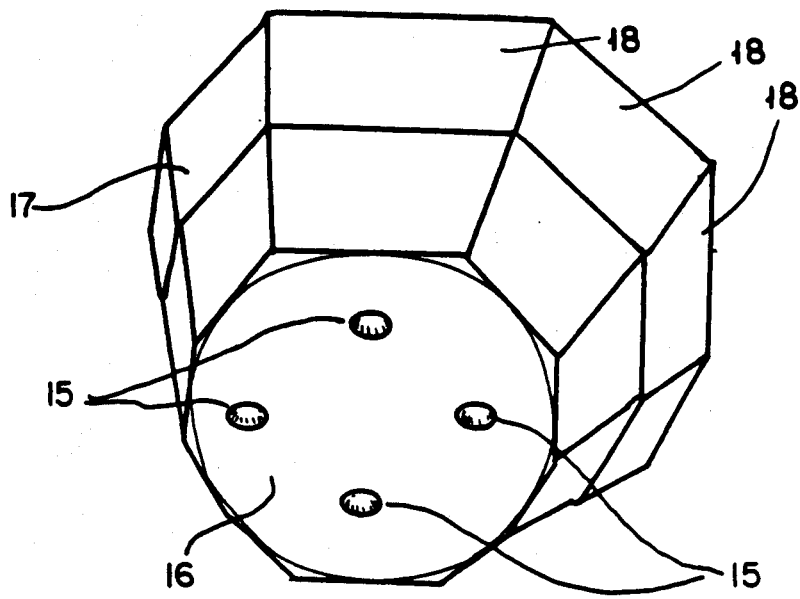
FIG. 2 is a perspective view of a container for use with the weighing apparatus of FIG. 1.

Referring now to the drawings wherein similar numerals have been used to indicate like parts, there is shown therein a weighing apparatus generally indicated at 10 according to the invention. The apparatus 10 comprises a housing 11 having a weighing plate 12 which is connected to an electrically controlled conventional load cell 13 located within the housing 11. The plate 12 has formed thereon a plurality of upwardly projecting protrusions 14 which engage in corresponding recesses 15 formed on the base 16 of a container 17. The container 17 is in use located on the plate 12 with the protrusions 14 engaged in the recesses 15, and thus the container is readily retained in place on the plate 12, and will not be displaced from the plate 12 by swabs being thrown into the container.

The container 17 which is preferably disposable is formed having ten sides 18, corresponding to the number of swabs which will be deposited in the container. In addition, the interior of the container is formed having ten compartments, defined by ribs or flanges (not shown) extending from the center of the container, each compartment corresponding with a respective side 18 of the container. Thus, when a number of swabs are located in the container 17, one to each compartment, the number of swabs in the container being ten or less, can be readily counted without having to handle the swabs.

The apparatus 10 is provided with wheels (not shown) to enable it to be readily moved, and also has a peripheral rubber buffer member 20 fixed thereon.

Figure 3:
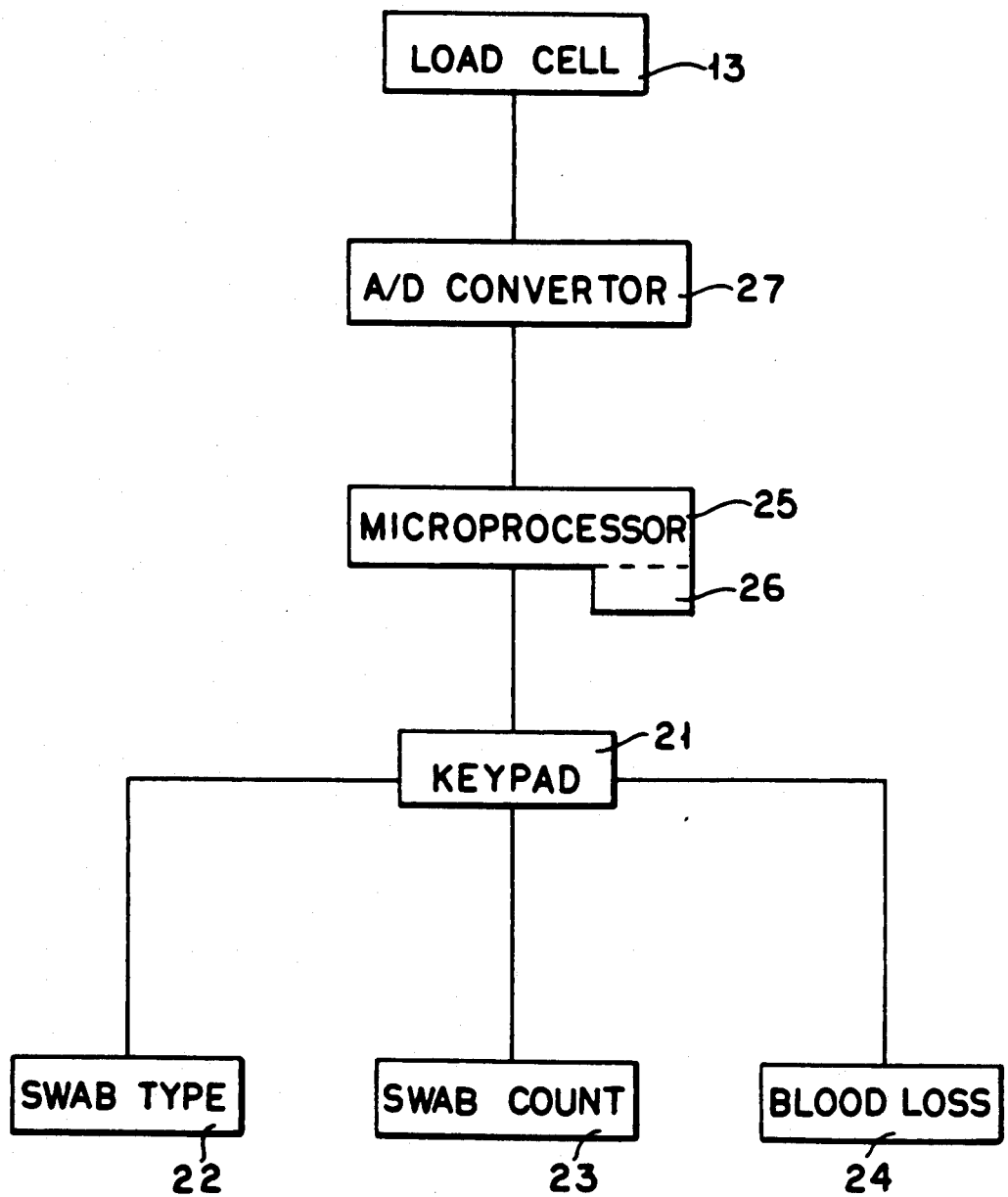
FIG. 3 is a block diagram of the control system of the weighing means.

The front wall 19 of the housing 11 has a keypad 21 and visual displays 22, 23 and 24 which are electrically corrected to a microprocessor 25 mounted within the apparatus, as generally indicated in FIG. 3. The visual displays 22, 23 and 24 are provided to enable a visual indication of swab type, swab count, and blood loss as will now be described in greater detail. The microprocessor 25 also a memory 26, and the electrical output signal (a Voltage) from the conventional load cell 13 is converted to a digital signal by an analogue/digital converter 27 the digital signal being processed by the microprocessor 25. It will be appreciated that the apparatus will operate from a battery or mains electrical power supply.

The program sequence stored in microprocessor 25, for providing a continuing visual display output of the swab count and blood loss, as determined by the number and weight of used swabs deposited in the container 17 is described below. The program uses memory addresses of; SWABWT (swab weight), SWABCNT (swab count), BLOODLOSS, and OLDWT (old weight). As well as controlling the visual displays 22, 23 and 24, the keypad 21 can be used to input into the microprocessor the swab type which is in use, i.e. this may be a swab of 5, 10, 20, 40 or 120 gms. or other weight. When the program is initialised the four memory addresses noted above are set to zero. The program steps are as follows:

1. Input the number 40 onto the SWAB TYPE display (i.e. this is the start-up swab type). Store this number in the SWABWT memory location.

2. Take 5 readings from the load cell (measured in mV), average these and store the result in memory location 'OLDWT'. (i.e. this sets the start-up load cell output as the base reading from which subsequent weight increases are measured).

3. Monitor the keypad to see if a different swab type (i.e. 5, 10, 20, 40, 120) has been entered by the operator. If this happens then display the new selected option on the SWAB TYPE display. Also store this into SWABWT memory location. Continue to monitor the keypad throughout normal running, on an interrupt basis.

4. Monitor the load cell output signal. Take five readings and calculate average of these, assign this to variable $X_1$. Take another five readings and average, assign this value to variable $X_2$. Repeat this step until $X_1$ and $X_2$ are equal.

5. If $X_1$ and $X_2$ are equal subtract the value of $X_1$ (at step 4 above) from the previously recorded OLDWT.

6. If and only if this difference (at step 5 above) is greater than 3mV (or some other specified tolerance level), then accept it as the 'new weight' level and proceed to step 7. If not then continue to cycle through step 4.

7. Increase the SWABCOUNT by one: display the new swabcount, and index the memory location SWABCNT by one.

8. Convert voltage value obtained in step 6 to the gram equivalent.

9. Subtract this new gram weight (step 8) from the currently selected SWAB TYPE. If this difference value is positive then add this difference to the current BLOOD LOSS display and redisplay the new total. Store the new total in memory location BLOODLOSS.

10. If difference value at step 9 is not greater then do not change the BLOOD LOSS display or stored value.

This allows counting of, say, a 10 gram swab when a type 40 gm has been selected.

11. Store the new load cell output (as recorded at step 4) in the OLDWT memory location.

12. Go back to step 4 and continue to monitor the loadcell output, with the new OLDWT as the base reference.

Figure 4:
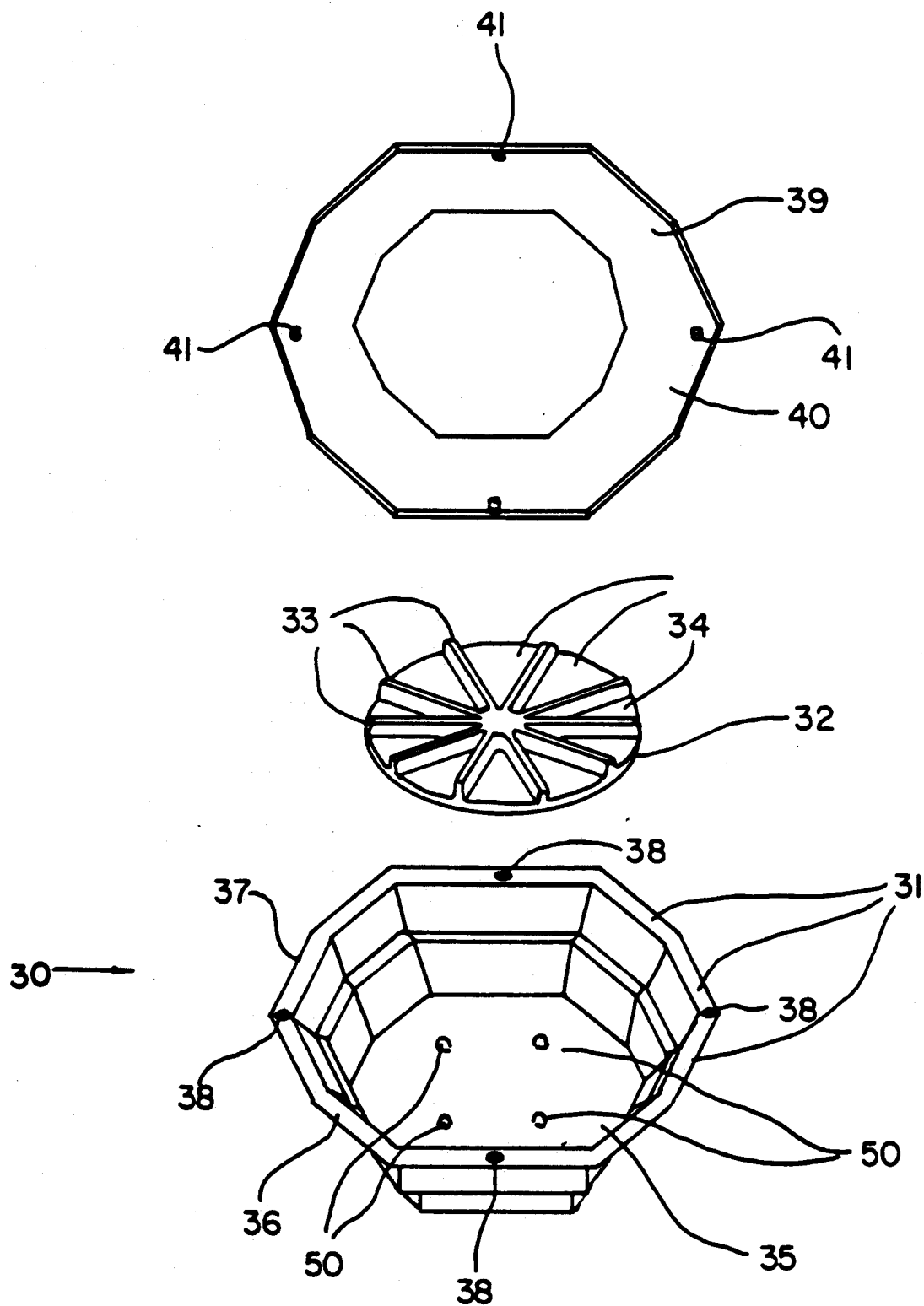
FIG. 4 is an exploded view of another embodiment of a container according to the invention.

In FIG. 4 there is shown another embodiment of a disposable container generally indicated at 30. The container 30 which has a predetermined number of sides 31 (in this example 10 sides) is of a lightweight plastics material which may be translucent or transparent. A plastics insert 32 is formed having a plurality (in this example 10) of radially extending upstanding wall portions 33 which define between them radial recesses 34. The insert 32 fits snugly into the base 35 of the container. The top rim 36 of the container comprises a peripheral flange 37 having four recesses 38 formed therein. A lid 39 is provided to close the container the underside 40 of the lid 39 having four depending lugs 41 each of which is an interference fit in a respective one of the recesses 38 to enable the lid to be secured on the container.

This radial arrangement of recesses 38 enables swabs to be readily located in the container 30 with the minimum level of handling and enables the number of swabs to be quickly counted.

Moreover, it will be appreciated that rather than use the separate insert 32, the base 35 of the container 30 may be formed having radial wall portions similar to those of the insert 32, to define recesses in the base of the container. Alternatively the insert 32 may be fixed to or integrally formed on the base 35 of the container.

It will be appreciated that the number of radial recesses in the base of the container may vary, however, the number is preferably a multiple of five.

The base 35 of the container 30 may also have recesses 50 similar to those in the container of FIG. 2 to enable the container to be engaged on a weighing apparatus as described herein.

Figure 1:
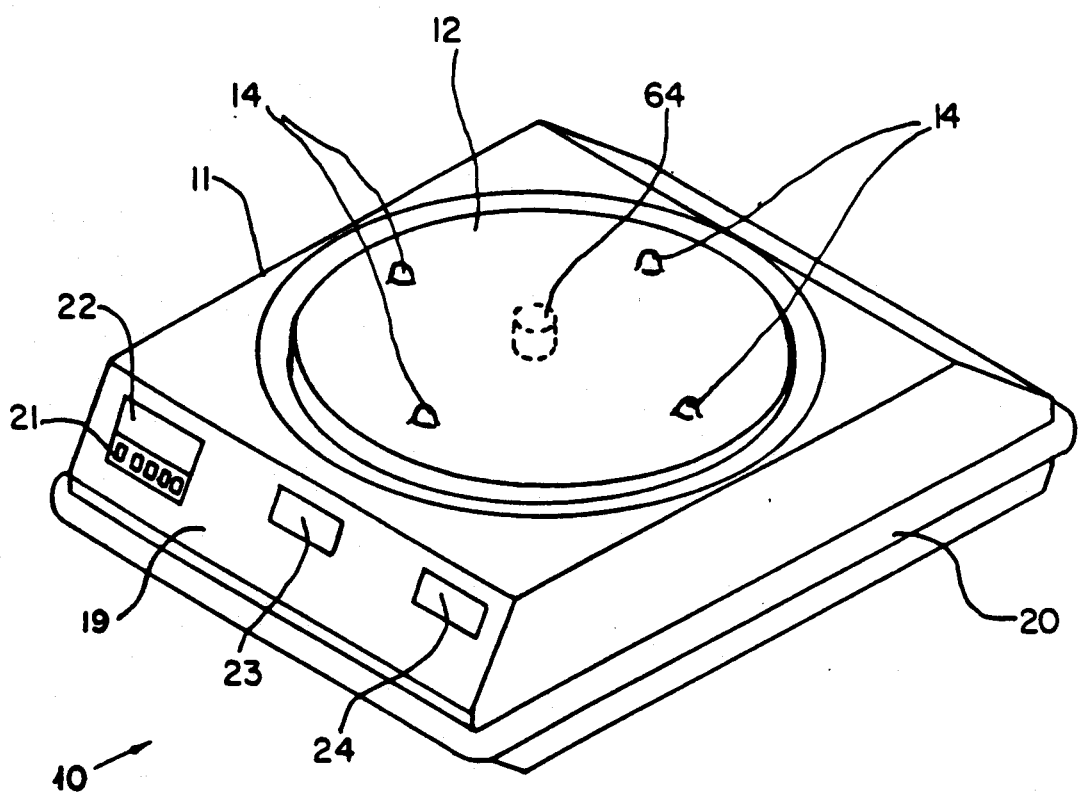
FIG. 1 is a perspective view of a weighing apparatus according to the invention.

In FIG. 5 there is shown another embodiment of a container generally indicated at 60 according to the invention. As shown, the container 60 which is of a transparent or translucent plastics material comprises five compartments 61 defined between upstanding wall members 62 and disposed radially about a central pillar 63. The container 60 is integrally moulded in conventional manner. The container 60 also has a recess (not shown) formed on its underside and located below the central pillar 63, the recess provided to accommodate a locating lug 64, which is fixed to the plate 12 as indicated in dotted outline in FIG. 1. Clearly, the protrusions 14 are not provided on the plate 12 when the container 60 is to be used. The container 60 is provided with a lid 65 to close the container once it has been filled with five used swabs, one to each compartment.

This invention thus provides an apparatus which will readily provide an indication of the number of swabs deposited in the container and which will also provide an indication of the accumulated blood loss as determined by the weight of the swabs. Once the container has effectively been filled by depositing in it ten swabs, it may be sealed with a lid and then disposed of. The invention minimises the handling of the swabs which is highly desirable.

It will be appreciated that the load cell will be adjusted in conventional manner to provide a zero weight indication when the empty container is located on the weighing plate 12.

I claim:

1. A medical swab weighing apparatus, comprising a container into which used swabs may be deposited during the course of an operation, and a weighing means on which the container is removably support and which provides an electrical output signal whose value is dependent upon the instantaneous total weight of the container and contents, the weighing means having means for storing the weight of a dry swab and program means responsive to the stored weight of a dry swab and the electrical output signal for calculating and displaying, each time a swab is deposited in the container, the total weight of blood absorbed in used swabs deposited in the container and the total number of swabs deposited in the container.

2. An apparatus as claimed in claim 1, wherein said weighing means comprises a housing having a weighing plate connected to an electrically controlled load cell mounted within the housing, the output signal from the load cell being fed to a microprocessor via an analogue to digital converter.

3. An apparatus as claimed in claim 2, wherein a keypad is provided on the housing for controlling the operation of the microprocessor.

4. An apparatus as claimed in claim 2, wherein the housing is provided with suitable visual displays for indicating the weight of blood loss and the number of swabs in the container means.

5. An apparatus as claimed in claim 1, wherein the container means comprises a container having a plurality of radially disposed compartments each for receiving a used swab.

6. An apparatus as claimed in claim 5, wherein the container comprises a translucent or transparent plastics material.

7. An apparatus as claimed in claim 5, wherein the container and weighing means have complementary interengaging surfaces to locate and retain the container on the weighing means.

8. An apparatus as claimed in claim 2, wherein the housing has a rubber buffer member fixed around its sides.

* * * * *